(12) United States Patent
Shi et al.

(10) Patent No.: US 8,975,418 B2
(45) Date of Patent: Mar. 10, 2015

(54) PROCESS FOR PREPARING 6-IODO-2-OXINDOLE

(71) Applicants: Wenjian Shi, Suzhou (CN); Yanli Song, Shanghai (CN); Yuhui Bao, Shanghai (CN); Jun Lu, Shanghai (CN); Yao Huang, Shanghai (CN); Dirk Weber, Mainz (DE)

(72) Inventors: Wenjian Shi, Suzhou (CN); Yanli Song, Shanghai (CN); Yuhui Bao, Shanghai (CN); Jun Lu, Shanghai (CN); Yao Huang, Shanghai (CN); Dirk Weber, Mainz (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/013,097

(22) Filed: Aug. 29, 2013

(65) Prior Publication Data
US 2014/0066634 A1     Mar. 6, 2014

(30) Foreign Application Priority Data
Sep. 4, 2012     (WO) ................ PCT/CN2012/080952

(51) Int. Cl.
*C07C 69/78*     (2006.01)
*C07D 209/12*     (2006.01)
*C07D 209/36*     (2006.01)
*C07D 209/34*     (2006.01)
*C07C 207/04*     (2006.01)
*C07C 201/12*     (2006.01)
*C07D 209/42*     (2006.01)
*C07C 205/56*     (2006.01)

(52) U.S. Cl.
CPC ............ *C07D 209/34* (2013.01); *C07C 207/04* (2013.01); *C07C 201/12* (2013.01); *C07D 209/42* (2013.01); *C07C 69/78* (2013.01); *C07D 209/12* (2013.01); *C07C 205/56* (2013.01)
USPC .......................... 548/484; 548/492; 560/103

(58) Field of Classification Search
CPC ..... C07C 69/78; C07D 209/36; C07D 209/12
USPC .................................. 548/484, 492; 560/103
See application file for complete search history.

(56) References Cited

U.S. PATENT DOCUMENTS

2014/0066634 A1     3/2014     Shi et al.

FOREIGN PATENT DOCUMENTS

| EP | 1310486 A1 | 5/2003 |
|---|---|---|
| JP | 2011207859 A | 10/2011 |
| WO | 9623770 A1 | 8/1996 |
| WO | 2007008985 A2 | 1/2007 |

OTHER PUBLICATIONS

International Search Report and Written Opinion for PCT/EP2013/068094 mailed Nov. 14, 2013.

*Primary Examiner* — Shawquia Jackson
(74) *Attorney, Agent, or Firm* — Michael P. Morris; Mary-Ellen M. Devlin

(57) ABSTRACT

Disclosed is a method for the synthesis of 6-iodo-2-oxindole useful as intermediate in the manufacture of pharmaceutically active ingredients. Also disclosed is a novel intermediate used in the synthesis of this compound.

19 Claims, No Drawings

PROCESS FOR PREPARING 6-IODO-2-OXINDOLE

TECHNICAL FIELD

This invention relates to a novel method for the synthesis of 6-iodo-2-oxindole useful as intermediate in the manufacture of pharmaceutically active ingredients.

BACKGROUND 6-iodo-2-oxindole is an important intermediate for the production of pharmaceutically active ingredients. The synthesis of this intermediate has been described in the literature before and is quite challenging. Therefore there is a strong demand for efficient methods to manufacture 6-iodo-2-oxindole in the high quality needed for pharmaceutical intermediates.

In current literature several routes to manufacture 6-iodo-2-oxindole have been described.

WO 2007008985 describes the synthesis of 6-iodo-2-oxindole via catalytic electrophilic aromatic iodination of 6-bromo-2-oxindole using sodium iodide in the presence of a copper catalyst (Scheme 1). The disadvantage of this approach is the fact that 6-bromo-2-oxindole is not directly commercially available as a bulk chemical. Additionally the use of large amounts of a copper catalyst, the use of dioxane as solvent and several reaction additives which are only available on laboratory scale disqualify this approach for commercial production.

Scheme 1. Electrophilic iodination of 6-bromo-2-oxindole

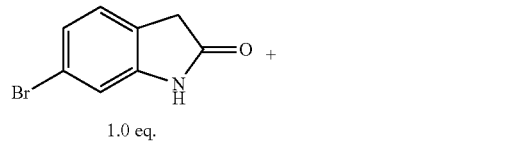

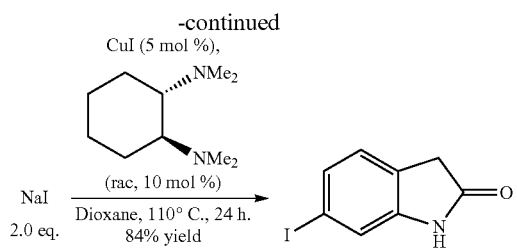

JP 2011207859 describes the synthesis of 6-iodo-2-oxindole from 1,4-diiodo-2-nitro-benzene via two steps of reaction. The disadvantage of this process is again the use of a starting material that is not commercially available on larger scale, therefore this process is also disqualified for use for commercial production of 6-iodo-2-oxindole (Scheme 2).

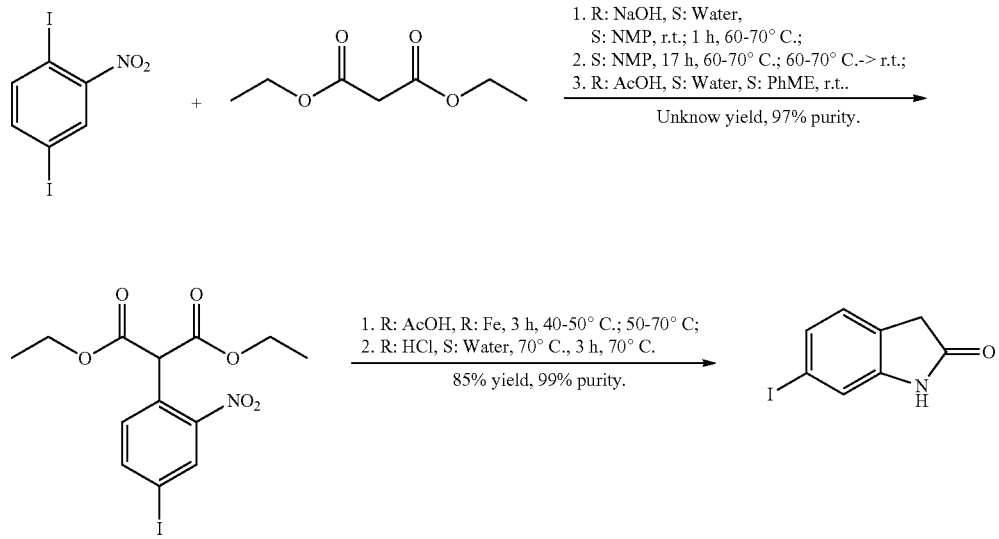

Therefore there is a strong need for a novel process to manufacture 6-iodo-2-oxindole, which allows to use commercially available bulk chemicals as starting materials and which renders the desired product in high quality and good chemical yield.

DESCRIPTION OF THE INVENTION

The present invention provides an efficient process for the manufacture of 6-iodo-2-oxindole in high quality starting from commercially available 2-chloro-nitrobenzene as starting material in the steps as described herein below.

It has been found that the very cheap starting material 2-chloro-nitrobenzene, after selective iodination to 2-chloro-5-iodonitrobenzene could be used in this reaction, whereas the process described in JP 2011207859 (Scheme 2) shows the use of rather instable 2,5-diiodonitrobenzene is necessary for the successful application of the follow-up steps. Within the present invention it has been shown, that the more stable and easier to produce intermediate 2-chloro-5-iodonitrobenzene can be successfully used in the downstream steps, for example alkylation with a malonic acid dialkyl ester (preferably dimethylmalonate or diethylmalonate) and successively be transformed to 6-iodo-2-oxindole in very high purity.

Thus, the present invention relates to a process for preparing 6-iodo-2-oxindole comprising:

a) iodination of 2-chloro-nitrobenzene to form 2-chloro-5-iodonitrobenzene, b) reacting 2-chloro-5-iodonitrobenzene with malonic acid dialkyl ester, preferably malonic acid dimethyl ester (dimethylmalonate) or malonic acid diethyl ester (diethylmalonate), to form 2-(4-iodo-2-nitrobenzene)-dialkylmalonate, and c) performing a reduction, cyclisation and decarboxylation to form 6-iodo-2-oxindole.

A general process for preparing 6-iodo-2-oxindole is outlined in Scheme 3a. In one embodiment, the present invention is directed to the general multi-step synthetic method for preparing 6-iodo-2-oxindole as set forth in Scheme 3a below. In other embodiments, the invention is directed to each of the individual steps of Scheme 3a and any combination of two or more successive steps of Scheme 3a. The invention may also be directed to the intermediate compounds, e.g. as set forth in Scheme 3a.

Scheme 3a. Process for the manufacture of 6-iodo-2-oxindole according to the invention:

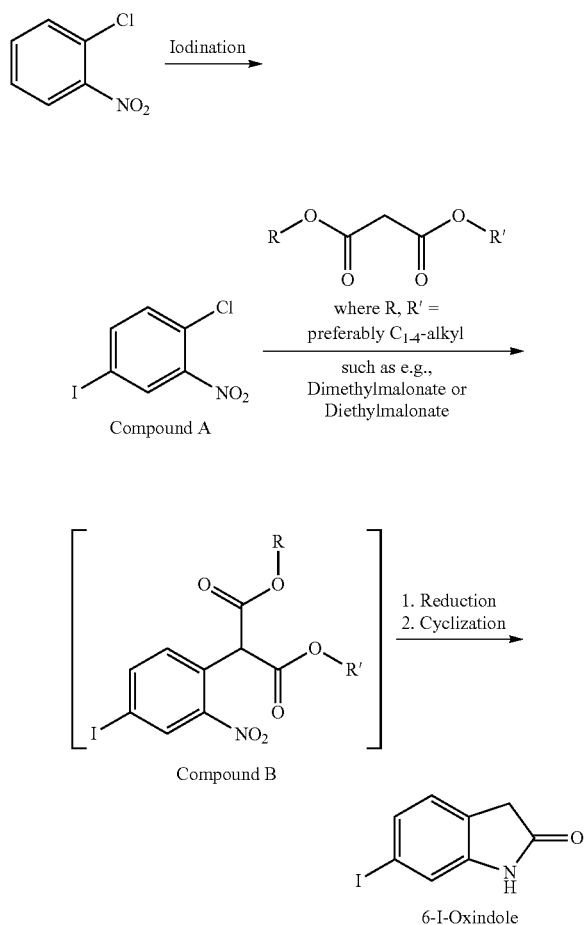

In certain more detailed embodiments of the invention, the present invention relates to the process and/or the individual process steps substantially as disclosed according to following Scheme 3b:

Scheme 3b. Process for the manufacture of 6-iodo-2-oxindole according to the invention:

In the first step of the process according to the present invention, 2-chloro-nitrobenzene is oxidatively iodinated to form 2-chloro-5-iodonitrobenzene (Compound A) by using a suitable iodination agent, for example a mixture of molecular iodine and sodium periodate, preferably in the presence of a suitable acid (such as e.g. (concentrated) sulfuric acid) and preferably in a suitable solvent (such as e.g. a mixture of (glacial) acetic acid and acetic anhydride). Preferably the iodination reaction is carried out at elevated temperature.

In the second step, 2-chloro-5-iodonitrobenzene (Compound A) is selectively alkylated with for example a malonic acid dialkyl ester, preferably dimethyl malonate or diethylamlonate, in a nucleophilic substitution reaction to form the intermediate 2-(4-iodo-2-nitrobenzene)-dialkylmalonate, preferably 2-(4-iodo-2-nitrobenzene)-dimethylmalonate or -diethylmalonate (Compound B), preferably by using standard basic conditions (such as e.g. suitable metal alkanolate, e.g. sodium alkanolate, such as e.g. sodium methanolate or sodium ethanolate as base) and in a suitable solvent (such as e.g. N,N-dimethylacetamide, DMAc). Preferably the alklyation reaction is carried out from reduced to elevated temperature. Preferably, the choice of the appropriate metal alkanolate (particularly sodium alkanolate) may be based on the choice of the respective alkyl ester.

In the next step(s), 2-(4-iodo-2-nitrobenzene)-dialkylmalonate (Compound B) is treated under reductive, cyclisative and decarboxylative conditions. For example, using a suitable reducing agent, such as e.g. a tin(II)-based reducing agent (preferably SnCl$_2$), or Fe in acidic media, catalytic hydrogenation, or the like, in a suitable solvent (such as e.g. ethanol), preferably followed by further steps (which may be in any order) comprising cyclization, decarboxylation, and, optionally if required, further reduction of the resulting intermediate(s) or mixture of intermediates, to yield 6-iodo-2-oxindol. The resulting intermediate(s) or mixture of intermediates obtained from the steps above may be repeatedly treated under suitable conditions to induce full cyclisation, reduction and decarboxylation to form 6-iodo-2-oxindole. The cyclization and/or decarboxylation is preferably conducted under acid conditions (such as e.g. using aqueous HCl) in a suitable solvent (such as e.g. aqueous ethanol). Preferably the reduction reaction and/or the cyclization and/or the decarboxylation reaction are carried out at elevated temperature.

Optionally, the last steps (reduction/cyclization/decarboxylation) described above can be run without the necessity to isolate the corresponding intermediates, for example 1-hydroxy-6-iodo-2-oxo-2,3-dihydro-1H-indole-3-carboxylic acid alkyl (e.g. methyl or ethyl) ester, so the intermediates can be handled in solution e.g. to reduce operation complexity.

Further, optionally, the second and third steps described above can be run without the necessity to isolate the resulting intermediate, 2-(4-iodo-2-nitrobenzene)-dialkylmalonate, so also this intermediate can be handled in solution e.g. to reduce operation complexity.

In a further alternative, optionally, even the steps described in the second step and the in the last steps together, can be run without the necessity to isolate the corresponding intermediates, so also these intermediates can be handled in solutions to reduce operation complexity.

In particular embodimental aspects of the invention, reference may be made to the following aspects 1-22 according to the invention:

1. A method of preparing a compound of formula (B)

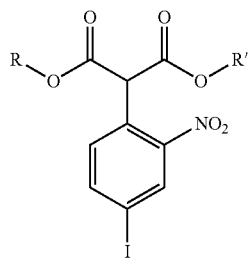
(B)

wherein R and R' may be the same or different, and are each independently selected from C$_{1-4}$-alkyl (e.g. methyl, ethyl, propyl, isopropyl, butyl, isobutyl, sec-butyl, or tert-butyl), particularly C$_{1-2}$-alkyl such as methyl or ethyl, or R and R' together are a —CH$_2$—, —CH$_2$CH$_2$— or —C(CH$_3$)$_2$— group, preferably R and R' are the same and are each methyl or ethyl, said method comprising reacting 2-chloro-5-iodonitrobenzene having the formula (A)

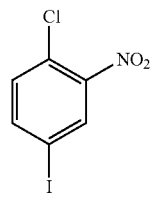
(A)

with an open chain or cyclic malonic acid dialkyl ester of formula

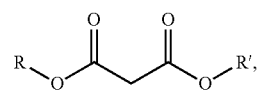

wherein R and R' are defined as in formula (B), preferably in the presence of a suitable base, to form a compound of formula (B).

2. The method according to aspect 1, wherein a suitable base is sodium methanolate or sodium ethanolate.

3. The method according to aspect 1 or 2, wherein the reaction is conducted in a suitable solvent or mixture of solvents, preferably comprising N,N-dimethylacetamide.

4. A method of preparing a 6-iodo-2-oxindole having the formula

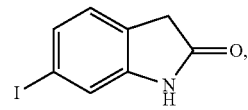 [SMILES: O=C1Cc2ccc(I)cc2N1]

said method preferably comprising the method according to aspect 1, 2 or 3, and further comprising a) reducing a compound of formula (B), preferably in the presence of a suitable reducing agent; and b) cyclizing, optionally further reducing and decarboxylating the resulting intermediates or mixture of intermediates, preferably in the presence of a suitable acid, to form 6-iodo-2-oxindole.

5. The method according to aspect 4, wherein a suitable reducing agent preferably in a) is a tin(II)-based reducing agent (preferably SnCl$_2$).

6. The method according to aspect 4 or 5, wherein the reduction reaction in a) is conducted in a suitable solvent or mixture of solvents, preferably comprising ethanol.

7. The method according to aspect 4, wherein a suitable acid in b) is aqueous HCl.

8. The method according to aspect 4 or 7, wherein the cyclization and/or decarboxylation and/or optional further reduction reaction in b) is conducted in a suitable solvent or mixture of solvents, preferably comprising ethanol.

9. The method according to any one of aspects 1 to 8, wherein the intermediate compound of formula (B) is either (in one embodiment) isolated or (in another embodiment) not isolated.

10. The method according to any one of aspects 4 to 8, wherein an intermediate compound obtained from step a) of aspect 4 is either (in one embodiment) isolated or (in another embodiment) not isolated.

11. The method according to any one of aspects 4 to 8, wherein an intermediate compound obtained from any reactions of step b) of aspect 4 is either (in one embodiment) isolated or (in another embodiment) not isolated.

12. The method according to any one of aspects 1 to 8, wherein the intermediate compound of formula (B) and/or an intermediate compound obtained from step a) of aspect 4 and/or an intermediate compound obtained from any reactions of step b) of aspect 4 is/are either (in one embodiment) isolated or (in another embodiment) not isolated.

13. The method according to any one of aspects 1 to 12, wherein R and R' are the same and are preferably methyl or ethyl.

14. The method according to any one of aspects 1 to 13, wherein the compound of formula (A) is prepared by iodination of 2-chloro-nitrobenzene.

15. The method according to aspect 14, wherein the system I$_2$/NaIO$_4$ preferably in the presence of a suitable acid (e.g. sulfuric acid) is used for iodination.

16. The method according to aspect 14 or 15, wherein the reaction is conducted in a suitable solvent or mixture of solvents, preferably comprising acetic acid and acetic anhydride.

17. A compound of formula

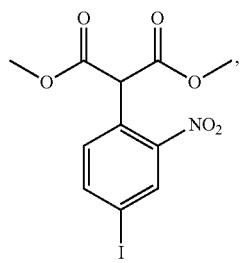

for example either in isolated form or in solution.

18. A compound of formula

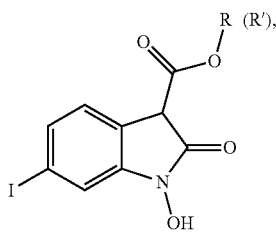

wherein R, R' is as defined above (e.g. methyl or ethyl), for example either in isolated form or in solution.

19. A method of preparing a 6-iodo-2-oxindole having the formula

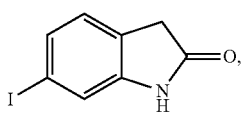

said method preferably comprising the method according to aspect 1, 2, 3, 4a or 4b (cyclizing), and further comprising reducing and/or decarboxylating a compound of formula

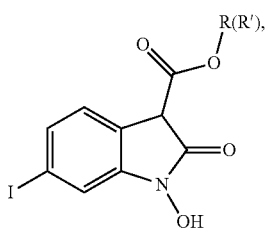

wherein R, R' is as defined above, preferably in the presence of a suitable reducing agent (e.g. SnCl$_2$) and/or preferably in the presence of a suitable acid (e.g. HCl), preferably in a suitable solvent or mixture of solvents, preferably comprising ethanol, to form 6-iodo-2-oxindole.

20. A method of preparing a 6-iodo-2-oxindole having the formula

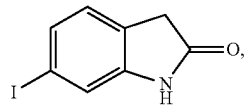

said method preferably comprising the method according to aspect 1, 2, 3, 4a or 4b (cyclizing), and further comprising decarboxylating a compound of formula

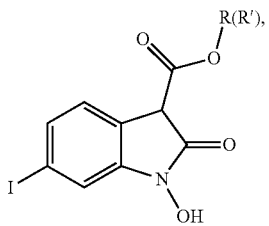

wherein R, R' is as defined above, preferably in the presence of a suitable acid (e.g. HCl), preferably in a suitable solvent or mixture of solvents, preferably comprising ethanol, to form a compound of formula

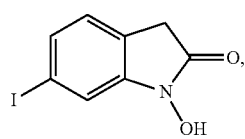 [SMILES: O=C1Cc2ccc(I)cc2N1O]

and reducing the obtained 1N-hydroxy-6-iodo-2-oxindole to form 6-iodo-2-oxindole, preferably in the presence of a suitable reducing agent, preferably in a suitable solvent or mixture of solvents, preferably comprising ethanol, to form 6-iodo-2-oxindole.

21. A method of preparing a 6-iodo-2-oxindole having the formula

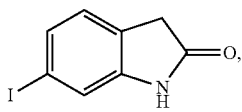

said method preferably comprising the method according to aspect 1, 2, 3, 4a or 4b (cyclizing, decarboxylating), and further comprising
reducing a compound of formula

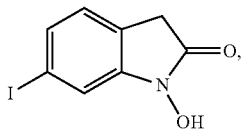 [SMILES: O=C1Cc2ccc(I)cc2N1O]

preferably in the presence of a suitable reducing agent and preferably in the presence of a suitable acid, preferably in a suitable solvent or mixture of solvents, preferably comprising ethanol, to form 6-iodo-2-oxindole.

22. A compound of formula

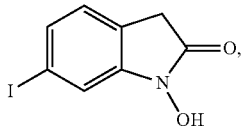

for example either in isolated form or in solution.

The reactants used in the synthetic schemes described below may be obtained either as described herein, or if not described herein, are themselves either commercially available or may be prepared from commercially available materials by methods known in the art.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by High Pressure Liquid Chromatography (HPLC) or Thin Layer Chromatography, if desired.

EXAMPLES

In order that this invention be more fully understood, the following examples are set forth. These examples are for the purpose of illustrating preferred embodiments of this invention, and are not to be construed as limiting the scope of the invention in any way. All commercial products are bought from SCRC, except sodium methylate and sodium ethylate which are from Acros.

Exemplary HPLC method (UV length: 254 nm): The separation is performed on an Xbridge™ C18 3.5 μm 4.6×100 mm, Waters at a column temperature of 30° C. A mixture of Water with 0.1% formic acid (pH 2.7) and 100% acetonitrie is used as mobile phase (80/20-30/70). The method run time is set at 20 min applying a mobile phase flow rate of 1.0 mL/min. The injection volume is 1.0 μL.

Preparation of 2-chloro-5-iodonitrobenzene

To a jacketed reactor, acetic acid (450 mL) and acetic anhydride (225 mL) is charged at 10° C. Then, to the above mixture, $NaIO_4$ powder (97.2 g) and Iodine (77.2 g) is added under stirring. While keep internal temperature at below 30° C., conc. $H_2SO_4$ (720 mL) is added dropwise. Then, 2-chloronitrobenzene (Rt=11.11 min) is added in one portion, and heat the mixture gradually to 64° C. The resulting mixture continues to be stirred for usually at least 2 hours until process monitor shows almost complete conversion. Then, the mixture is cooled down to room temperature, and transferred slowly into another jacketed reactor with pre-cooled cold $Na_2SO_3$ solution (250 g $Na_2SO_3$ in 2000 mL water). Collect the wet cake by filtration and wash the cake with water (450 mL×2), then purification of the cake with n-heptane crystallization to afford 2-chloro-5-iodonitrobenzene in 62% yield and 98% HPLC purity (Rt=15.75 min).

$^1$H NMR (400 MHz, $CDCl_3$) δ 7.26-7.29 (m, 1H), 7.81-7.84 (dd, J=8.4, 2.0 Hz, 1H), 8.17-8.16 (d, J=2.0 Hz, 1H); $^{13}$C NMR (100 MHz, $CDCl_3$) δ 90.5, 127.0, 133.2, 134.1, 142.1, 148.3; MS (ESI): m/z 282.9 (M).

Preparation of 2-(4-iodo-2-nitrobenzene)-dimethlymalonate

To a jacketed reactor, N,N-dimethylacetamide (DMAc) (960 mL) and sodium methylate (NaOMe) powder (77.8 g) is charged at 20° C. Dimethyl malonate (191 g) is added dropwise into the above mixture while keeping internal temperature at around 10° C. After finishing addition, warm up the mixture to 20° C., and continue to stir for another 10 minutes. Then, 2-chloro-5-iodonitrobenzene (136 g) is added in one portion, and heat the mixture to 78° C. and stir for usually at least 2.5 hours until process monitor shows almost complete conversion. The resulting mixture is cooled down to 20° C., and it is quenched by 2 N cold aq. HCl solution (1440 mL). Then, the mixture is stirred for another 1 hour. Collect the solid by filtration and wash the solid with water (500 mL) to afford 2-(4-iodo-2-nitrobenzene)-dimethlymalonate (146 g) as pale yellow solid in 80% yield and 97% HPLC purity (Rt=13.9 min).

$^1$H NMR (400 MHz, $CDCl_3$) δ 3.79 (s, 6H), 5.26 (s, 1H), 7.25-7.27 (m, 1H), 7.95-7.98 (dd, J=8.3, 1.8 Hz, 1H), 8.36-8.37 (d, J=1.8 Hz, 1H); $^{13}$C NMR (100 MHz, $CDCl_3$) δ 53.3, 53.6, 93.4, 127.4, 132.8, 133.8, 142.4, 148.9, 167.1; MS (ESI): m/z 378.96 (M+1).

Preparation of 6-iodo-2-oxindole

To a jacketed reactor, 2-(4-iodo-2-nitrobenzene)-dimethlymalonate (130 g) is charged at 20° C., followed by ethanol (600 mL). Then, to the above solution the first portion of $SnCl_2.2H_2O$ (193.5 g) powder is added, and the resulting mixture is heated to 70° C. and stirred for 1 hour. The second portion of $SnCl_2.2H_2O$ (193.5 g) is added, the mixture is stirred usually at least 0.5 hour until process monitor shows almost complete conversion. Then, heat the resulting mixture to 80° C. and add 36% aq. HCl solution (360 mL) during 0.5 hour. The mixture is stirred for at least 2.5 hours until process monitor shows almost complete conversion. Then, to the mixture water (550 mL) is added and the resulting mixture is cooled down to 20° C. Collect the solid by filtration and wash the solid with water (500 mL) to afford the crude 6-iodo-2-oxindole. Then, it is purified by crystallization with acetic acid (HOAc) (560 mL), and followed by washing with 3 N aq. HCl solution (480 mL) to afford the 6-iodo-2-oxindole in 62% yield and 99% HPLC purity (Rt=7.45 min).

$^1$H NMR (400 MHz, DMSO) δ 10.42 (5, 1H), 7.29-7.27 (dd, J=8.0, 1.6 Hz, 1H,), 7.11 (d, J=1.6 Hz, 1H), 7.02-7.00 (d, J=8.0 Hz, 1H); $^{13}$C NMR (100 MHz, CDCl$_3$) δ 175.9, 145.3, 129.6, 126.4, 125.7, 117.4, 92.2, 35.4; MS (ESI): m/z 260.1 (M+1).

Preparation of 6-iodo-2-oxindole from 2-chloro-5-iodonitrobenzene and diethyl malonate without Isolation of Intermediates To a jacketed reactor, N,N-dimethylacetamide (DMAc) (120 mL) and sodium ethylate (NaOEt) powder (12.1 g) is charged at 20° C. Diethylmalonate (28.8 g) is added dropwise into the above mixture while keeping internal temperature at around 10° C. After finishing addition, warm up the mixture to 20° C., and continue to stir for another 10 minutes. Then, 2-chloro-5-iodonitrobenzene (17 g) is added in one portion, and heat the mixture to 78° C. and stir for usually at least 2.5 hours until process monitor shows almost complete conversion. The resulting mixture is cooled down to 20° C., and it is quenched by 2 N cold aq. HCl solution (180 mL). The bottom yellow oil was transferred to a jacket reactor with ethanol (92 mL) in it. Then, to the above solution the first portion of SnCl$_2$.2H$_2$O (30 g) powder is added, and the resulting mixture is heated to 70° C. and stirred for 1 hour. The second portion of SnCl$_2$.2H$_2$O (30 g) is added, the mixture is stirred usually at least 0.5 hour until process monitor shows almost complete conversion. Then, heat the resulting mixture to 80° C. and add 36% aq. HCl solution (60 mL) during 0.5 hour. The mixture is stirred for at least 2.5 hours until process monitor shows almost complete conversion. Then, to the mixture water (90 mL) is added and the resulting mixture is cooled down to 20° C. Collect the solid by filtration and wash the solid with water (250 mL) to afford the crude 6-iodo-2-oxindole. Then, it is purified by crystallization with acetic acid (HOAc) (110 mL), and followed by washing with 3 N aq. HCl solution (80 mL) to afford the 6-iodo-2-oxindole in 53% yield and 99% HPLC purity (Rt=7.45 min).

$^1$H NMR (400 MHz, DMSO) δ10.42 (S, 1H), 7.29-7.27 (dd, J=8.0, 1.6 Hz, 1H,), 7.11 (d, J=1.6 Hz, 1H), 7.02-7.00 (d, J=8.0 Hz, 1H); $^{13}$C NMR (100 MHz, CDCl$_3$) δ 175.9, 145.3, 129.6, 126.4, 125.7, 117.4, 92.2, 35.4; MS (ESI): m/z 260.1 (M+1).

What is claimed is:

1. A method of preparing a compound of formula (B)

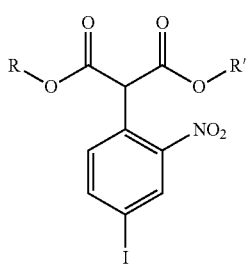

(B)

wherein R and R' may be the same or different, and are each independently selected from $C_{1-4}$-alkyl (e.g. methyl, ethyl, propyl, isopropyl, butyl, isobutyl, sec-butyl, or tert-butyl), or R and R' together are a —CH$_2$—, —CH$_2$CH$_2$— or —C(CH$_3$)$_2$— group, said method comprising reacting 2-chloro-5-iodonitrobenzene of formula (A)

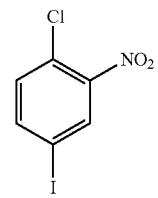

(A)

with an open chain or cyclic malonic acid dialkyl ester of formula

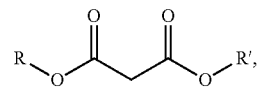

wherein R and R' are defined as in formula (B), in the presence of a suitable base, to form a compound of formula (B).

2. The method according to claim 1, wherein a suitable base is sodium methanolate or sodium ethanolate.

3. The method according to claim 1, wherein the reaction is conducted in a suitable solvent or mixture of solvents.

4. The method according to claim 1 further comprising preparing a 6-iodo-2-oxindole of formula

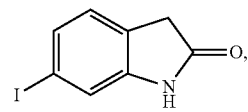

by
a) reducing a compound of formula (B) with the aid of a suitable reducing agent; and
b) cyclizing and decarboxylating to form 6-iodo-2-oxindole.

5. The method according to claim 4, wherein the suitable reducing agent is a tin(II)-based reducing agent.

6. The method according to claim 4, wherein the reduction reaction in a) is conducted in a suitable solvent or mixture of solvents.

7. The method according to claim 4, wherein aqueous HCl is used in step b).

8. The method according to claim 4, wherein the cyclization and/or decarboxylation and/or further reduction reaction in b) is conducted in a suitable solvent or mixture of solvents.

9. The method according to claim 1, wherein the intermediate compound of formula (B) is isolated.

10. The method according to claim 4, wherein the intermediate compound obtained from step a) of claim 4 is isolated.

11. The method according to claim 4, wherein the intermediate compound obtained from any reactions of step b) of claim 4 is isolated.

12. The method according to claim 4, wherein the intermediate compound of formula (B) and/or the intermediate compound obtained from step a) of claim 4 is/are isolated.

13. The method according to claim 1, wherein R and R' are the same and are ethyl or methyl.

14. The method according to claim 1, wherein the compound of formula (A) is prepared by iodination of 2-chloronitrobenzene.

15. The method according to claim 14, wherein the system $I_2/NaIO_4$ is used for said iodination.

16. The method according to claim 14, wherein the reaction is conducted in a suitable solvent or mixture of solvents.

17. A compound of formula

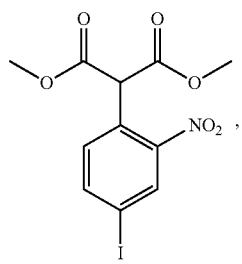

either in isolated form or in solution.

18. A compound of formula

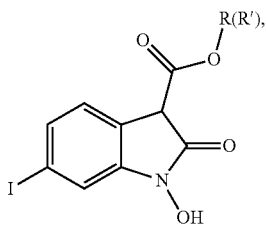

wherein R and R' may be the same or different, and are each independently selected from $C_{1-4}$-alkyl (e.g. methyl, ethyl, propyl, isopropyl, butyl, isobutyl, sec-butyl, or tert-butyl), or R and R' together are a —CH$_2$—, —CH$_2$CH$_2$— or —C(CH$_3$)$_2$— group, either in isolated form or in solution.

19. A compound of formula

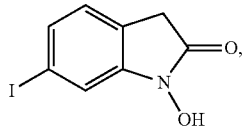 [SMILES: O=C1Cc2ccc(I)cc2N1O]

either in isolated form or in solution.

* * * * *